United States Patent
Chang

(10) Patent No.: US 9,867,734 B2
(45) Date of Patent: Jan. 16, 2018

(54) DEVICE FOR REDUCING SNORING

(71) Applicant: Chi-Fu Chang, Taichung (TW)

(72) Inventor: Chi-Fu Chang, Taichung (TW)

(*) Notice: Subject to any disclaimer, the term of this patent is extended or adjusted under 35 U.S.C. 154(b) by 733 days.

(21) Appl. No.: 14/472,731

(22) Filed: Aug. 29, 2014

(65) Prior Publication Data
US 2016/0030231 A1  Feb. 4, 2016

(30) Foreign Application Priority Data
Aug. 4, 2014  (TW) .............................. 103126561 A

(51) Int. Cl.
*A61F 5/56* (2006.01)
(52) U.S. Cl.
CPC .................................. *A61F 5/566* (2013.01)
(58) Field of Classification Search
CPC ....... A61F 5/566; A61F 2005/563; A61F 5/56
See application file for complete search history.

(56) References Cited

U.S. PATENT DOCUMENTS

| | | | | |
|---|---|---|---|---|
| 8,127,769 B2* | 3/2012 | Walker | ................... | A61F 5/566 128/848 |
| 2004/0211430 A1* | 10/2004 | Pivovarov | ............... | A61F 5/566 128/848 |
| 2005/0092331 A1* | 5/2005 | D'Agosto | ............... | A61F 5/566 128/859 |
| 2010/0132720 A1* | 6/2010 | Razmovski | ............. | A61F 5/566 128/848 |

* cited by examiner

*Primary Examiner* — Tarla Patel
(74) *Attorney, Agent, or Firm* — Lynette Wylie; Apex Juris, pllc.

(57) ABSTRACT

A device for reducing snoring includes a ventilation tube having an air passageway therein and a first opening and a second opening at opposite ends of the air passageway, wherein a diameter of the first end is greater than that of the second opening, and a holding member connected to the ventilation tube at an end having the first opening. Put the device of the present invention in mouth may hold a normal shape of the upper respiratory tract while the user is sleeping and ventilate the air without obstruction while the user is breathing, so the user would not snore in sleep to improve the quality of sleep.

8 Claims, 3 Drawing Sheets

DEVICE FOR REDUCING SNORING

The current application claims a foreign priority to the patent application of Taiwan No. 103126561 filed on Aug. 4, 2014.

BACKGROUND OF THE INVENTION

1. Technical Field

The present invention relates generally to a device to help sleeping, and more particularly to a device to increase sleeping quality and reduce snore.

2. Description of Related Art

Snoring is the common problem happing in sleeping. In the past, people think snore in sleep is nothing to health but the noise. However, some researches taught us snore is an index of sleep apnea syndrome, and the sleep apnea syndrome may cause cardiovascular diseases and apoplexy.

Why people snore in sleeping? Snoring is a physiology problem. Men who snore usually have a narrow respiratory tract. In daytime, muscles of pharynx and larynx are contracted that may keep the respiratory tract open. However, when he/she lies on the bed to sleep at night, as shown in FIG. 1, the muscles are relaxed that the tongue 1 will move toward the throat 2 because of the gravity to narrow the upper respiratory tract. Therefore, breathing in will resonate soft palate 3. Something, the soft palate 3 obstructs the upper respiratory tract, and the breathing out air can't go out through nose 2a and stays in oral cavity 4. Once the pressure in the oral cavity 4 is too high, the air will be breaking out. That is snore.

In present days, there are three ways to treat snore which are: 1) Continuous-positive-airway pressure (CPAP); 2) Uvulopalatopharyngoplasty (UPPP); and 3) Mandibular advancing device (MAD). It is known that CPAP is the most effective on sleep apnea syndrome. However, there probably is no one can stand that mark, which patient has to wear it to sleep. UPPP is to cut off soft palate and uvula by surgical operation. The research found that only 50% patients no longer snore after surgery. MAD may help over 70% patients. However, people have to hold the device in the mouth that is is very uncomfortable. Sometime, people will feel pain on teeth, lower jaw, and mouth muscles because of the device.

BRIEF SUMMARY OF THE INVENTION

In view of the above, the primary objective of the present invention is to provide a method of setting a user interface of a remote control system, which shows the controllable electric appliances on the electronic device in an easier recognizable way.

The present invention provides a device for reducing snoring including a ventilation tube and a holding member. The ventilation tube has an air passageway therein and a first opening and a second opening at opposite ends of the air passageway, wherein a diameter of the first end is greater than that of the second opening. The holding member is connected to the ventilation tube at an end having the first opening.

Whereby, put the device of the present invention in mouth may hold a normal shape of the upper respiratory tract while the user is sleeping and ventilate the air without obstruction while the user is breathing, so the user would not snore in sleep to improve the quality of sleep.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
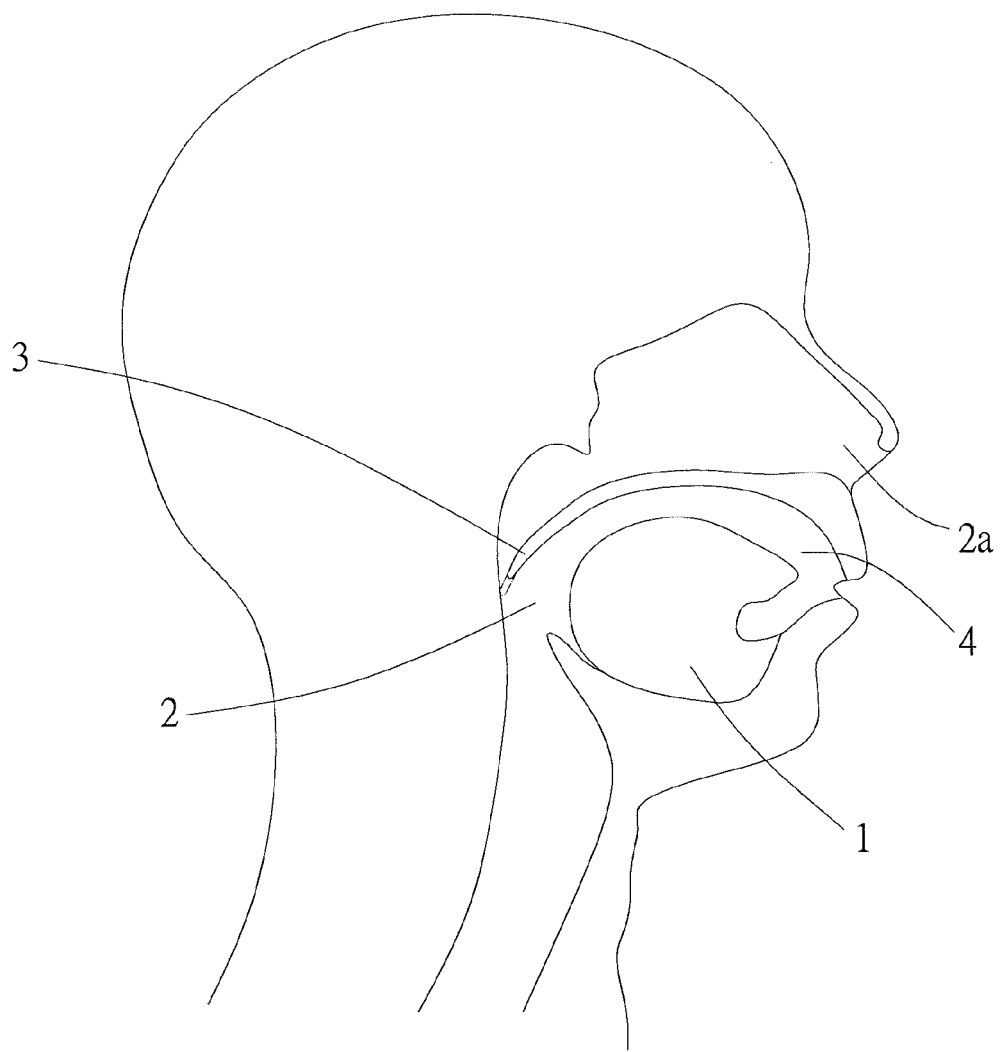
FIG. 1 is a sketch diagram of why people snore.
Figure 2:
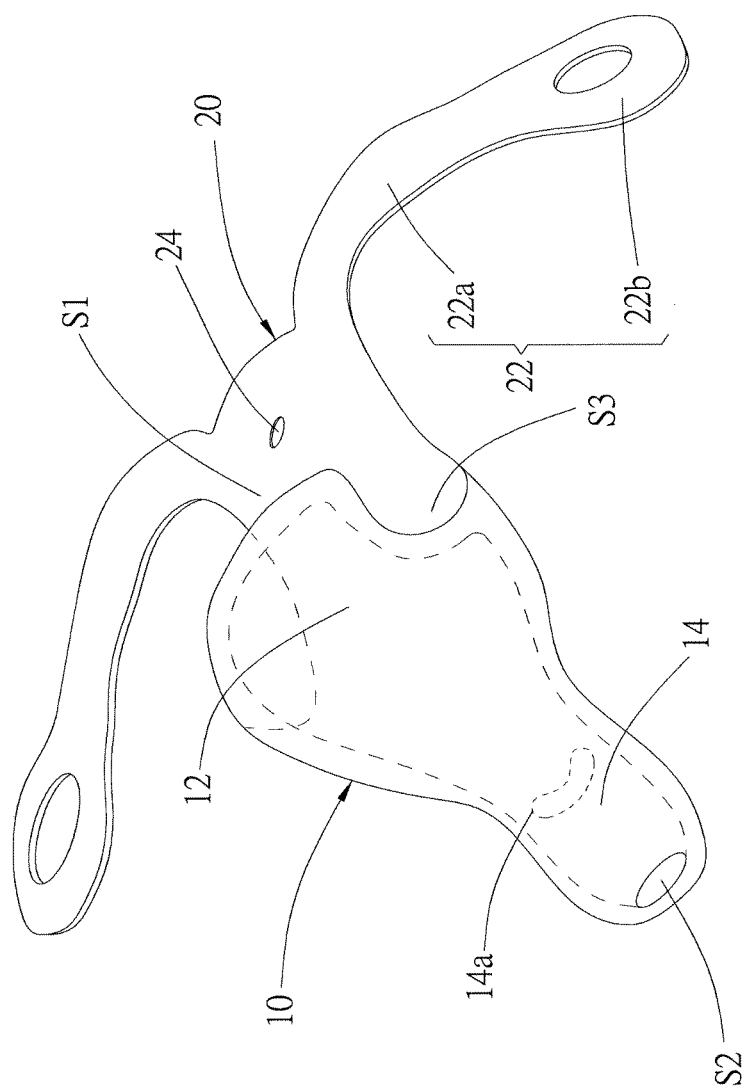
FIG. 2 is a perspective view of a preferred embodiment of the present invention.

As shown in FIG. 2, a device for reducing snoring of the preferred embodiment of the present invention includes a ventilation tube 10 and a holding member 20, wherein the ventilation tube 10 and the holding member 20 are made of silicon rubber, and made into a single element, therefore, the entire device is flexible.

The ventilation tube 10 has a first section 12 and a second section 14. The first section 12 and the second section 14 are connected together and have an air passageway therein. The ventilation tube 10 has a first opening S1 at an end of the first section 12 and a second opening S2 at an end of the second section 14. In other words, the first opening S1 and the second opening S2 are opposite ends of the air passageway.

A diameter the first section 12 gradually increases and then decreases from the end having the first opening S1 to an end connected to the second section 14, and a diameter of the entire second section 14 is constant. The diameter the first section 12 is greater than the diameter of the second section 14. In other words, the first section 12 has a bulged portion at middle thereof. The ventilation tube 10 further has two recesses S3 at the end of the first section 12 having the first opening S1, therefore two flexible pieces are formed between the recesses S3. The second section 14 is provided with a curved aperture 14a, which is communicated with the air passageway.

The holding member 20 is a Y-shaped member having a trunk and two branches 22. The trunk is connected to one of the flexible pieces of the ventilation tube 10, and the branches 22 each has an end connected to the trunk and extend in opposite directions. Each branch 22 has a band 22a and a tail portion 22b at a distal end of the band 22a, wherein a wide of the tail portion 22b is greater than that of the band 22a, and the tail portion is provided with a bore. The trunk is provided with a bore 24 for a wire (not shown) to fasten the device. This wire extends out of mouth while a user puts the device of the present invention in mouth, and is fastened to the clothing he/she wears to prevent the user from swallowing the device of the present invention in sleep.

Figure 3:
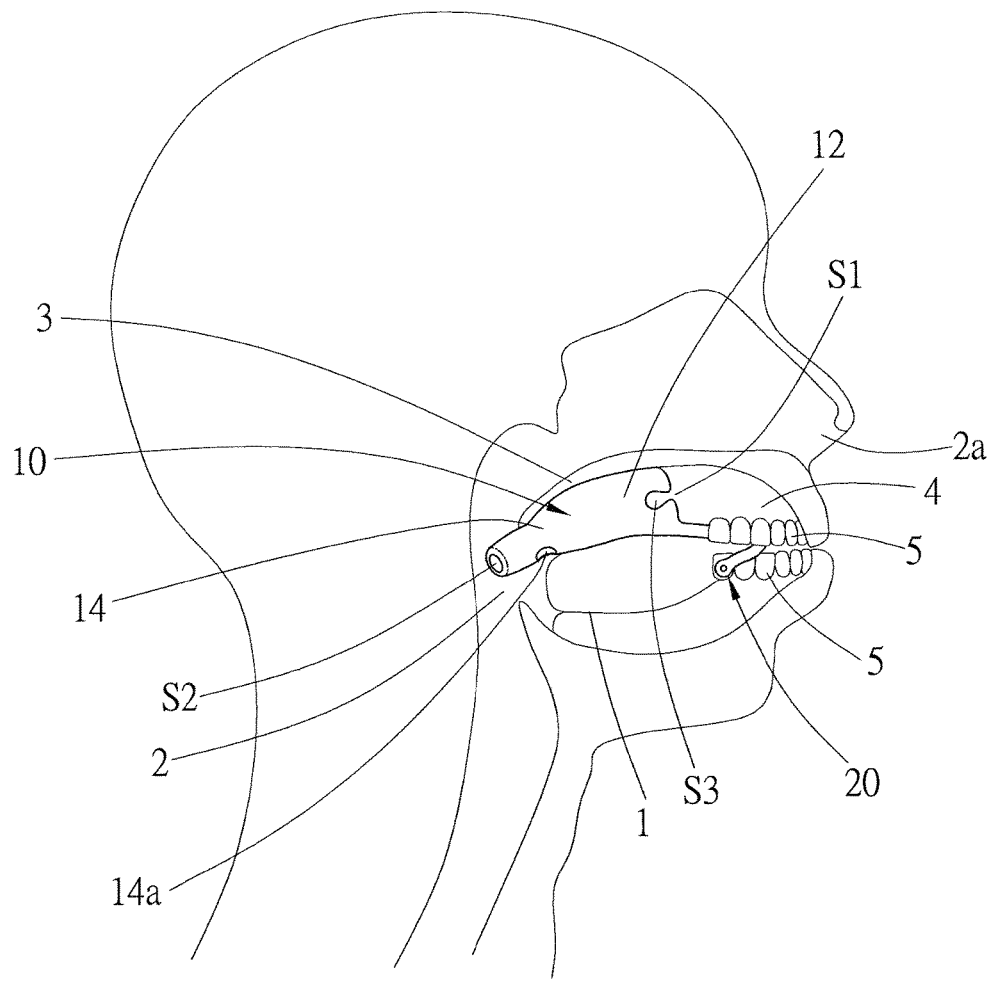
FIG. 3 is a sketch diagram, showing the device of the preferred embodiment of the present invention in human's mouth.

As shown in FIG. 3, the device of the present invention is put into human's oral cavity. Rubber silicon provides a friction between the device and tongue and palate, which holds the device at a predetermined position in the oral cavity, and precisely at a posterior part of tongue 1. The device of the present invention will slip to its desired position while the user put it in mouth.

The bulged portion of the first section 12 moves the soft palate 3 upwards to avoid the soft palate 3 from being resonated. Besides, the shape of the first section 12 just fits the palate to attach the entire first section 12 to the the palate that makes the user feel comfortable when using the device of the present invention. The recesses S3 make the second section 14 more flexible to be put in a small oral cavity. It makes most of people may use the device of the present invention.

The second section 14 is held at the posterior part of tongue 1 to avoid tongue 1 from obstructing upper respiratory tract. A length of the second section 14 is shorter than that of the first section 12 to reduce uncomfortable feeling when the device of the present invention is in mouth.

The holding member 20 is flexible and extendable because it is made of silicon rubber. The branches 22 of the holding member 20 extend to molar teeth to let the user bites the bands 22a, and left the tail portions 22b out of teeth. The function of the holding member 20 is to hold the device of the present invention in oral cavity.

As shown in FIG. 3, while the device of the present invention is put in the oral cavity 4, it keeps the upper respiratory tract to flow without obstruction so as to reduce the risk of snoring. Precisely, when the user is breathing in, the device would keep a diameter of the throat 2 to avoid the soft palate 3 being resonated. While the user is breathing out, the soft palate 3 is hold by the device of the present invention, so air could directly go out via nose 2a, and some air will go into the oral cavity 4 through the air passageway of the ventilation tube 10 (via the second opening S2 and the aperture 14a), and go through spaces between the ventilation tube 10 and a sidewall of the oral cavity 4 to go out via nose 2a. Therefore, snoring is stopped.

Sometime, the second opening S2 of the ventilation tube 10 will be obstructed because of phlegm the aperture 14a plays a second access of the air passageway of the ventilation tube 10 to let the device of the present invention still function normally.

In conclusion, the device of the present invention provides the ventilation tube 10 to hold a normal shape of the upper respiratory tract while the user is sleeping and ventilate the air without obstruction while the user is breathing, so the user would not snore in sleep to improve the quality of sleep.

It must be pointed out that the embodiments described above are only some preferred embodiments of the present invention. All equivalent structures which employ the concepts disclosed in this specification and the appended claims should fall within the scope of the present invention.

What is claimed is:

1. A device for reducing snoring, comprising:
   a ventilation tube having an air passageway therein and a first opening and a second opening at opposite ends of the air passageway, wherein a diameter of the first opening is greater than that of the second opening; and
   a holding member extending from a wall of the first opening of the ventilation tube;
   wherein the first opening and the second opening are adapted to be positioned in an oral cavity of a user;
   wherein the ventilation tube and the holding member are made of silicon rubber and are integral;
   wherein the ventilation tube has a bulged portion, which is adapted to move a soft palate of the user upwards
   wherein the ventilation tube is provided with two recesses recessed into a peripheral edge of the first opening towards the second opening, and the ventilation tube forms two flexible pieces on a lateral side of each of the recesses.

2. The device for reducing snoring of claim 1, wherein the ventilation tube has a first section and a second section, and a diameter of the first section is greater than that of the second section; the air passageway passes through the first section and the second section; and the first section has the first opening at an end thereof, and the second section has the second opening at an end thereof; the first section having the bulged portion.

3. The device for reducing snoring of claim 2, wherein the diameter of the first section increases and then decreases from the end having the first opening to an end connected to the second section.

4. The device for reducing snoring of claim 2, wherein the diameter of the entire second section is constant.

5. The device for reducing snoring of claim 2, wherein the second section of the ventilation tube is provided with an aperture communicated with the air passageway.

6. The device for reducing snoring of claim 2, wherein a length of the first section is longer than that of the second section.

7. The device for reducing snoring of claim 2, wherein the holding member has two branches connected to the first section of the ventilation tube, and each of the branches has a tail portion at a distal end thereof.

8. The device for reducing snoring of claim 7, wherein holding member further has a trunk; the trunk is connected to the first section of the ventilation tube, and the branches are connected to the trunk; and the trunk is provided with a bore for a wire being fastened thereto.

* * * * *